United States Patent [19]

Hesselgren

[11] 4,054,998

[45] Oct. 25, 1977

[54] METHOD AND APPARATUS FOR DISINFECTING FLUID MEDIUM REMOVED FROM THE ORAL CAVITY OF A HUMAN BEING

[76] Inventor: Sven-Gunnar Hesselgren, Angsholmen, S-170 11 Drottningholm, Sweden

[21] Appl. No.: 576,868

[22] Filed: May 12, 1975

[30] Foreign Application Priority Data

May 21, 1974 Sweden .............................. 7406728

[51] Int. Cl.² ........................ A61C 17/04; A61L 1/00; A61L 3/00
[52] U.S. Cl. ............................................. 32/33; 21/2; 21/53; 21/61; 21/74 R
[58] Field of Search ............................ 21/2, 121–127, 21/53, 58, 74 R, 61; 32/33; 239/53–57, 60; 55/279

[56] References Cited

U.S. PATENT DOCUMENTS

| 965,392 | 7/1910 | Meeker | 239/55 |
|---|---|---|---|
| 2,347,031 | 4/1944 | Cupery | 55/524 |
| 2,620,044 | 12/1952 | Fine et al. | 55/385 R |
| 2,638,180 | 5/1953 | Herkimer | 55/97 |
| 3,017,239 | 1/1962 | Rodman | 21/58 |
| 3,116,969 | 1/1964 | Coleman | 21/74 R |
| 3,224,434 | 12/1965 | Molomut et al. | 32/33 X |
| 3,371,985 | 3/1968 | Wyka | 21/121 |
| 3,516,160 | 6/1970 | Leffler | 32/33 |
| 3,591,328 | 7/1971 | Szappanyos et al. | 21/2 X |
| 3,595,607 | 7/1971 | Gores | 21/122 |
| 3,665,682 | 5/1972 | Ciavattoni et al. | 55/279 |
| 3,807,401 | 4/1974 | Riggle et al. | 32/33 X |

Primary Examiner—Morris O. Wolk
Assistant Examiner—Bradley Garris

[57] ABSTRACT

Method and means for continuously disinfecting a flow medium after its removal from an infectious area by passing it through a disinfecting zone in which a treating composition containing microbicidal substances is added to said flow medium.

10 Claims, 1 Drawing Figure

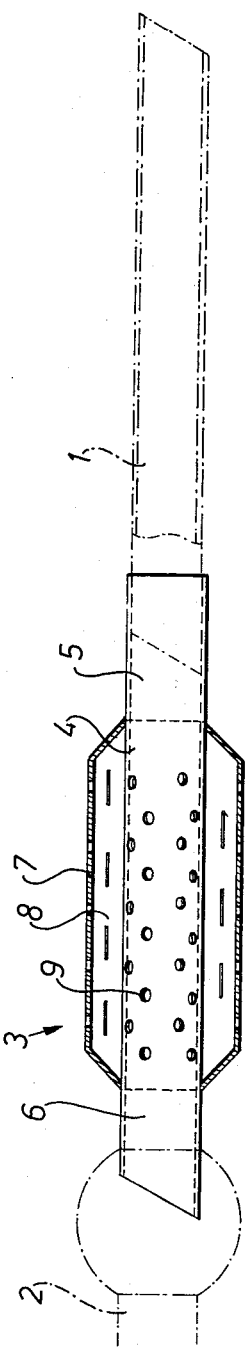

METHOD AND APPARATUS FOR DISINFECTING FLUID MEDIUM REMOVED FROM THE ORAL CAVITY OF A HUMAN BEING

BACKGROUND OF THE INVENTION

The present invention relates to a method and means for continuously and automatically disinfecting a flow medium removed from an infectious area. The invention can preferably be used for disinfecting any flow medium removed from an infectious area, but in the following will be described for the sake of simplicity as applied primarily to the field of odontology, without being in any way limited thereto.

In the field of odontology suction apparatus are widely used during treatment of a patient in order to remove saliva, blood and rinsing liquids as well as fragments of tooth, filling material and so on which collect during the treatment. The removal of this waste from the operation area, i.e. the teeth and the oral cavity, is essential to enable satisfactory surgical treatment of these areas.

Known suction apparatus used are generally provided with a replaceable mouthpiece, which is placed in the mouth to remove waste therefrom by means of suction. The mouth piece is fitted to a suction tube which is connected to an outlet via a separation vessel which is in turn placed in the operation or treatment room. The suction effect is generated by a motor (type vacuum-cleaner), which may be located either in the vicinity of the emptying point in the outlet or at some distance from the treating room. At its suction end the motor is connected to the system by an air hose. The air flow blown out from the motor is normally expelled directly out into the room where the motor is placed. Thus these prior methods are not satisfactory in view of hygienic regulations. As known the oral cavity, including teeth and saliva, contains considerable quantities of bacteria, fungus and virus even with healthy individuals, and if these are spread to regions other than the mouth or to other individuals, these may cause serious infections and allergies in persons so predisposed if frequently exposed. If there are serious centres of infection in the oral cavity, or when treating patients with infectious diseases such as tuberculosis or hepatitis, for example, the risks to the surroundings are alarming if the suction apparatus is used without any special precautions being taken. When the suction apparatus is used during treatment of a patient, the infected waste material, which is primarily in liquid form, is transported through the suction mouthpiece and suction tube to the outlet into which the waste is directly emptied. However, when mixed with the waste liquid, the suction air forms an aerosol containing quantities of microorganisms from the oral cavity, which is carried by the air flow through the air tube to the suction motor and the air exit on this. Thus the surroundings of the motor will be constantly subjected to an infected aerosol which will be mixed with the air breathed by persons on the premises even a long time after the suction means has been in use. Experiments performed to eliminate the spread of infection in this way by applying a bacteria filter which catches the infectious matter in the blow-out part of the motor have given negative results. After using the suction means for a short time the filters have become saturated and the resistance has therefore become too great for the driving motor, resulting in disturbed functioning and finally a break-down of the motor. The situation proves simply but convincingly the existence of an aereosol deriving from the infected waste.

In order to improve hygienic conditions, therefore, the suction equipment is nowadays rinsed with a water-soluble disinfectant as a matter of routine, at best after completion of each treatment. Generally, the disinfection is reduced to once a day and is performed when the last patient for the day has been treated. It is clear from what has been said above that no efficient and reliable decontamination is effected by sporadic efforts, and that the suction system must be continuously provided with microbicidal substances during the entire time the suction means is in function in order to fulfil reasonable requirements for protection of personnel and other persons in the vicinity.

One object of the present invention is therefore to eliminate the above mentioned drawbacks and to avoid any risk for infection within the treating room.

A further object of the invention is to provide a suitable device for performing the above suggested method.

These objects, others and numerous advantages will be set forth and apparent from the following description of the invention.

SUMMARY OF THE INVENTION

According to the present method a flow medium, preferably close to the suction point, is brought to pass a disinfecting zone in which the flow medium is treated with a microbicide.

The flow medium may consist of an air flow or airborne liquid flow which, by means of suction, is brought to pass said disinfecting zone and is here subjected to the action of a treating composition primarily containing microbicidal substances and possibly also surface active dirt-dissolving substances and/or anti-corrosion inhibitors and deodorants.

The treating composition is suitably applied in the disinfecting zone by surface application in a section of a through-flow channel passed by the flow medium.

Surface application may be effected by painting or spraying a composition, possibly including an adhesive, sticking component, in the disinfecting zone concerned. The components may alternatively be baked into a gel which is applied on the contact surface.

Another alternative is for the composition to be embedded in a carrier, preferably a porous carrier, which is either provided in the intended application point in the through-flow channel or can be manufactured separately in the form of a sleeve-shaped body which can easily be inserted into the through-flow channel.

Full details of the present invention follows herein and will be seen in connection with the accompanying drawing.

In the drawing a suction mouthpiece intended for application in the oral cavity is designated 1. The mouthpiece 1 is connected via a suction tube 2 to a suction source, not shown. In the embodiment shown in the drawing a disinfection means 3 is arranged between the mouthpiece 1 and the tube 2. This means 3 consists of a through-flow tube 4 of such dimensions that its two end sections 5, 6 can easily be applied to the mouthpiece 1 and the tube 2, respectively; either by pushing the ends 5, 6 of the tube 4 into or over the ends of the mouthpiece 1 and tube 2, respectively. Along at least a part of the total length of the through-flow tube 4 is an outer casing 7 having somewhat larger diameter than that of the tube 4 and the space 8 thus formed between the outer casing 7 and the tube 4 contains treating composition which, as well as microbicidal substances, may also contain anti-corrosion inhibitors, tensides and deodorants. Within the region covered by the outer casing 7 the tube 4 is provided with perforations 9, the grain size of the composition in the space 8 being larger than said perforations.

The means shown in the drawing thus consists of a container containing the water-soluble treating composition and is placed at the rear section of the mouthpiece, between the mouthpiece and its connection to the suction tube. In the example shown the device is composed substantially of two parts, namely the through-flow tube which has substantially the same dimension as the mouthpiece, and the outer casing which surrounds the through-suction tube. The means is easily fitted by insertion both into the suction mouthpiece and the suction tube. The through-flow tube is partially provided with small perforations, only within the part surrounded by the casing. The casing is slightly larger than the through-flow tube so that a small space is formed between the two parts and in this space the treating composition is placed, the grain size of the composition being larger than the perforations in the through-flow tube.

When the suction apparatus is in function, the liquid flowing through partially dissolves suitable quantities of the water-soluble microbicide which is quickly mixed with the departing waste and the infected aerosol arising in the suction tube. The fact that the microbicidal solution will be included in the aerosol results in a very intimate contact occurring between the despersed micro-organisms and the bacteria-killing substance. The exposure time for inactivation of the micro-organisms is therefore extremely short and complete decontamination takes place with full reliability during the transportation process through the tubes.

When the suction apparatus is not being used the microbicide is not dissolved either, but only when the apparatus is in use. The means is therefore economically advantageous in use. Another advantage with the means described is that it saves extra work since it requires little supervision once it has been applied. It may be provided with a colour indicator, for example, to indicate that the microbicide has been completely dissolved, the indicator being clearly visible through the outer casing which is preferably made of transparent material. The means can be designed with advantage for use once only and be disposed of in its entirely when the microbicide has been used up.

The means can be designed so that it does not impede handling of the mouthpiece for assisting personnel. It may consist of the same material, for example, as the disposable suction means to which it is connected.

As well as microbicidal substances, the disinfecting zone may also containing cleansing and surface active substances to keep the suction system clean as well as inhibitors to protect against corrosion and the treating composition might also include deodorants.

Suitable microbicides may include chloramine, sodium hypochlorite, chlorinated trisodium phosphate with potassium bromide (K-644), formaldehyde, glutaraldehyde, etc.. The microbicide need not necessarily consist of solid substances but may even comprise microbicides in liquid form. By placing a suitable carrier in the disinfecting zone such as a tampon, felt, gel or the like saturated with or baked into a solution of the microbicide in question, substantially any type of microbicide can be used. The treating composition may also be enclosed in permeable material.

As mentioned above, the invention is not limited to the embodiment shown in the drawing but can be modified in many ways within the scope of the following claims.

In its simplest application the treating composition may exist in the form of a solution and be applied in the disinfection zone by painting, spraying or the like. For this purpose it may be advantageous if the composition also contains an adhesive or sticking component.

Alternatively the treating composition may be applied on the appropriate parts of the suction equipment during manufacture, and these parts may suitably be made easily exchangeable. When being used in the odontology field, therefore, the treating composition can easily be applied during manufacture of the saliva mouthpiece which is replaced between each patient, the mouthpiece being provided on the inside with such a disinfecting zone.

The treating composition may also be applied on a porous carrier provided in the through-flow channel inside the disinfecting zone, this porous carrier perhaps being designed to continuously give off a certain quantity of the composition embedded therein. This porous carrier may either constitute a part of the through-flow channel itself or it may be designed to be detachably secured in the through-flow channel. For this purpose the carrier may be shaped to be inserted, for example in the form of a sleeve, and consist of a cardboard, flet or plastic sleeve impregnated with the treating composition. The treating composition may suitably exist in the form of a water-soluble salt in the carrier, thus making it non-perishable. The carrier may also be constructed in a manner known per se so that delayed release of the active substance is achieved. This can be achieved, for example, by compressing particles of plastic and the granular treating agent so that a plastic skeleton structure is formed in which the treating agent is embedded in channels and can be gradually bled out of these by the flow medium.

With respect to the field of application of the invention, it is finally emphasized that the invention can obviously also be used for cleaning operation areas during surgery, for example, i.e. general surgical operations on the human body and not only in the oral cavity.

Another field of application, for example, is the arrangement of such disinfecting zones in catheters for drawing off liquid, for example catheters leading to means for collecting urine, etc., where an uncontaminated material is connected.

What is claimed:

1. A method for continuously disinfecting a fluid medium, removed from the infectious area defined by the oral cavity of a human being comprising the steps of withdrawing said fluid medium as a flowing aerosol in a path from said infectious area under suction directly past a treatment zone, locating a treatment composition containing at least a microbiocidal substance within said treatment zone, said treatment composition being arranged about the periphery of said flow path of said aerosol in communication with said flowing aerosol without impeding the withdrawal of said fluid medium under suction or modifying the flow of aerosol, said suction acting to cause withdrawal of said microbiocidal substance from said composition and subsequent contact of said microbiocidal substance with said aerosol.

2. The method according to claim 1 wherein said treating composition includes additional active substances selected from the group consisting of anti-corrosion inhibitors and deodorants.

3. The method according to claim 1 wherein said treating composition comprises a solution.

4. The method according to claim 1 wherein the treatment composition is contained in a porous carrier and is adapted to continuously release a certain quantity of the microbiocidal substance embedded therein over a given time period.

5. Apparatus for continuously removing and disinfecting the infectious fluid medium from an infectious area defined by the oral cavity of a human being, comprising an axially open flow through tube, connection means at one end of said tube connected to means for insertion into and contact with the infectious area for the removal of said infectious fluid medium therefrom, means at the other end of said tube for connection to a source of suction, and a source of suction for removing said fluid medium in the form of a flowing aerosol, said tube being perforated along a section between its ends, said perforated section being surrounded by an enclosed housing secured at its ends to said tube, a treatment composition containing at least a microbiocidal substance arranged within said housing about the outer peripheral surface of said tube free of the flow path of said aerosol, said composition to be subjected to a suction to release said microbiocidal substance through said perforations in contact with the flowing aerosol without impeding the application of suction to said infectious area or modifying the flow of aerosol.

6. The apparatus according to claim 5 wherein said treatment composition comprises said microbiocidal substance and a solidifying gel, said microbiocidal substance being embedded therein.

7. The apparatus according to claim 5 wherein said treatment composition is granular.

8. The apparatus according to claim 5 including a porous carrier, said treatment composition being arranged on said porous carrier.

9. The apparatus according to claim 8 wherein said porous carrier is provided for insertion around the periphery of and arranged to be detachably secured to said tube.

10. The apparatus according to claim 8 wherein said carrier comprises an absorbent sleeve impregnated with the treatment composition.

* * * * *